United States Patent [19]
Endo

[11] Patent Number: 5,977,092
[45] Date of Patent: *Nov. 2, 1999

[54] DRUG FOR CURING/AMELIORATING CONCOMITANT SYNDROME OF TUMOR

[75] Inventor: Koichi Endo, Shizuoka-ken, Japan

[73] Assignee: Chugai Seiyaku Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/727,651

[22] PCT Filed: Apr. 18, 1995

[86] PCT No.: PCT/JP95/00754

§ 371 Date: Oct. 9, 1996

§ 102(e) Date: Oct. 9, 1996

[87] PCT Pub. No.: WO95/28162

PCT Pub. Date: Oct. 26, 1995

[30] Foreign Application Priority Data

Apr. 19, 1996 [JP] Japan ................................. 6-117356

[51] Int. Cl.$^6$ .................................................. A61K 31/59
[52] U.S. Cl. ............................................................ 514/167
[58] Field of Search ............................................... 514/167

*Primary Examiner*—Jerome D. Goldberg
*Attorney, Agent, or Firm*—Browdy and Neimark

[57] ABSTRACT

A drug for curing/ameliorating the concomitant syndrome of tumor which comprises a compound represented by the following general formula (I) as the active ingredient:

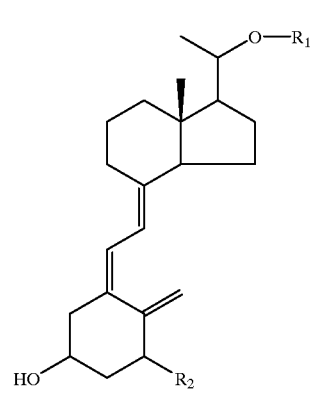

wherein $R_1$ represents an alkyl group having 1 to 10 carbon atoms and optionally substituted by one or more hydroxyl groups; and $R_2$ represents a hydrogen atom or a hydroxyl group; is disclosed.

This drug can be efficaciously employed in the treatment for the concomitant syndrome of tumor, in particular, cachexia or in the amelioration of the symptoms thereof.

7 Claims, No Drawings

DRUG FOR CURING/AMELIORATING CONCOMITANT SYNDROME OF TUMOR

TECHNICAL FIELD

This invention relates to a drug for curing/ameliorating the concomitant syndrome of tumor. More particularly, it relates to a drug for curing/ameliorating the concomitant syndrome of tumor which contains a vitamin D derivative as the active ingredient.

BACKGROUND ART

The term "concomitant syndrome of tumor" means symptoms accompanying various malignant tumors other than the direct symptoms, for example, cachexia, abnormalities in blood such as leukocytosis, failures in the homeostasis of bodily fluids typically exemplified by electrolyte abnormality, metabolic error such as hypoglycemia and diabetes, skin lesion, neurologic manifestation, serum protein abnormality, renal disorders, osteoarticular disorders, hyperenergia in association with the excessive secretion of adrenal cortex hormone, etc. These symptoms frequently arise in series. Among these symptoms, cachexia and electrolyte abnormality are the major ones which are known as the serious causes of the death of patients with cancer similar to respiratory failure, circulatory failure, digestive diseases, hemorrhage, systemic infection, etc.

The term "cachexia" means a systemically depressed state due to a chronic disease and its main symptoms include serious weight loss, inappetence and anemia. As typical examples of cachexia, there have been known cancerous cachexia, infectious cachexia, thyroid cachexia, etc.

Among all, it is considered that cancerous cachexia is a hindrance in the treatment for cancer, since it depresses the tolerance to chemotherapy or radiotherapy [Johanna T. Dwyer, Cancer, 43, 2077 (1979); Sarah S. Donaldson et al., Cancer, 43, 2036 (1979), etc].

To treat the concomitant syndrome of tumor, it has been a practice, for example, to administer various replenisher solutions and bone resorption inhibitors in the case of electrolyte abnormality. However these treatments are symptomatic ones which cannot suppress the production of causal substances originating in malignant tumors. Thus it is impossible to sufficiently cure the concomitant syndrome of tumor thereby.

Regarding the treatment of cachexia, on the other hand, it has been a practice to improve the nutritional status of patients by the administration of a high fat diet or a high saccharide diet, high caloric fluid therapy, blood transfusion, etc. However, these treatments serve merely as symptomatic therapy and can scarcely achieve any sufficient effect. Further, antitumor agents employed at present frequently induce serious side-effects and none of them is efficacious in the amelioration of cachexia. Accordingly, it has been urgently required to develop drugs for curing and ameliorating cachexia.

By the way, it has been known in general that some vitamin D derivatives show various physiological activities, for example, regulation of calcium metabolism, inhibition of the multiplication of tumor cells, induction of the differentiation of tumor cells, immunomodulation, etc. It is known that 22-oxa-vitamin D derivative having an oxygen atom at the 22-position, from among these vitamin D derivatives, exhibits only an extremely weak side-effect of inducing hypercalcemia which is commonly caused by other vitamin D compounds. Thus it is reported that this 22-oxa-vitamin D derivative is effective against psoriasis, secondary hyperparathyroidism, etc. (see, for example, Japanese Laid-Open Patent Publication No. Sho 63-183534 and Japanese Patent Publication No. Hei 6-86382). It is also known that this 22-oxa-vitamin D derivative has an antitumor effect. However, it has never been reported that this compound is effective against the concomitant syndrome of tumor such as cachexia.

An object of the present invention is to provide a drug which can cure the concomitant syndrome of tumor, in particular, cachexia or ameliorate the symptoms thereof.

Disclosure of the Invention

The present inventors have conducted extensive studies on a drug for curing/ameliorating the concomitant syndrome of tumor. As a result, they have successfully found out that a vitamin D derivative represented by the following general formula (I) is effective as a drug for curing/ameliorating the concomitant syndrome of tumor, thus completing the present invention:

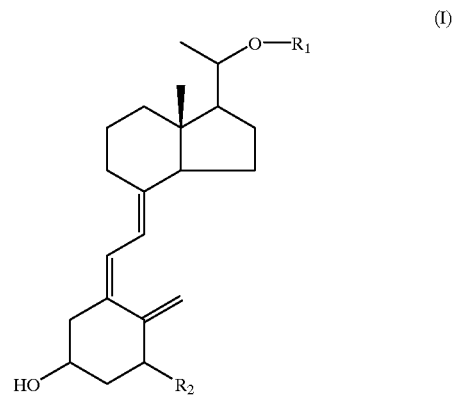

(I)

wherein $R_1$ represents an alkyl group having 1 to 10 carbon atoms and optionally substituted by one or more hydroxyl groups; and $R_2$ represents a hydrogen atom or a hydroxyl group.

Accordingly, the present invention provides a drug for curing/ameliorating the concomitant syndrome of tumor which comprises a compound represented by the following general formula (I) as the active ingredient:

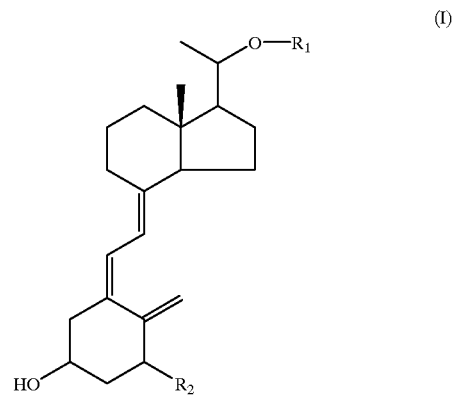

(I)

wherein $R_1$ represents an alkyl group having 1 to 10 carbon atoms and optionally substituted by one or more hydroxyl groups; and $R_2$ represents a hydrogen atom or a hydroxyl group.

Further, the present invention provides a drug for curing/ameliorating cachexia which comprises a compound represented by the following general formula (I) as the active ingredient:

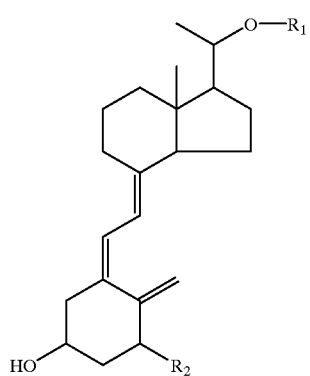

(I)

wherein $R_1$ represents an alkyl group having 1 to 10 carbon atoms and optionally substituted by one or more hydroxyl groups; and $R_2$ represents a hydrogen atom or a hydroxyl group.

Best Mode for Carrying out the Invention

The vitamin D derivative of the general formula (I) to be used in the present invention is a publicly known compound which is described in, for example, Japanese patent Publication No. Hei 3-74656. As stated in this reference, the vitamin D derivative of the general formula (I) can be synthesized with the use of, for example, pregnenolone or dehydroepiandrosterone as the starting material.

The alkyl group in the "alkyl group having 1 to 10 carbon atoms and optionally substituted by one or more hydroxyl groups" represented by $R_1$ in the general formula (I) of the present invention is a linear or branched alkyl group. Examples thereof include methyl, ethyl, n-propyl, i-propyl, n-butyl, i-butyl, s-butyl and t-butyl groups and pentyl, hexyl, heptyl, octyl, nonyl and decanyl groups. Preferable examples thereof include 3-methylbutyl, 3-ethylpentyl, 4-methylpentyl, 3-(n-propyl)hexyl, 4-ethylhexyl, 5-methylhexyl, 6-methylheptyl, 5-ethylheptyl and 4-(n-propyl)heptyl groups. Still preferably examples thereof include 3-methylbutyl, 3-ethylpentyl and 4-methylpentyl groups. Among all, a 3-methylbutyl group is the most desirable one.

The alkyl group as described above is optionally substituted with hydroxyl group(s). When substituted, the number of the hydroxyl substituents is, for example, 1,2 or 3, preferably 1 or 2 and still preferably 1. Examples of the alkyl group having 1 to 10 carbon atoms and substituted by one or more hydroxyl groups include 3-hydroxy-3-methylbutyl, 2-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-hydroxy-3-ethylpentyl, 2-hydroxy-3-ethylpentyl, 4-hydroxy-3-ethylpentyl, 2,3-dihydroxy-3-ethylpentyl, 2,4-dihydroxy-3-ethylpentyl, 3,4-dihydroxy-3-ethylpentyl, 4-hydroxy-4-methylpentyl, 3-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 3-hydroxy-3-(n-propyl)hexyl, 4-hydroxy-3-(n-propyl)hexyl, 2-hydroxy-3-(n-propyl)hexyl, 2,4-dihydroxy-3-(n-propyl)hexyl, 3,4-dihydroxy-3-(n-propyl)hexyl, 2,4-dihydroxy-3-(n-propyl) hexyl, 3-hydroxy-4-ethylhexyl, 4-hydroxy-4-ethylhexyl, 5-hydroxy-4-ethylhexyl, 3,4-dihydroxy-4-ethylhexyl, 3,5-dihydroxy-4-ethylhexyl, 4,5-dihydroxy-4-ethylhexyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-hydroxy-6-methylheptyl, 6-hydroxy-6-methylheptyl, 7-hydroxy-6-methylheptyl, 5,6-dihydroxy-6-methylheptyl, 5,7-dihydroxy-6-methylheptyl, 6,7-dihydroxy-6-methylheptyl, 4-hydroxy-5-ethylheptyl, 5-hydroxy-5-ethylheptyl, 6-hydroxy-5-ethylheptyl, 4,5-dihydroxy-5-ethylheptyl, 4,6-dihydroxy-5-ethylheptyl, 5,6-dihydroxy-5-ethylheptyl, 3-hydroxy-4-(n-propyl)heptyl, 4-hydroxy-4-(n-propyl)heptyl, 5-hydroxy-4-(n-propyl) heptyl, 3,4-dihydroxy-4-(n-propyl)heptyl, 3,5-dihydroxy-4-(n-propyl)heptyl and 4,5-dihydroxy-4-(n-propyl)heptyl groups. Preferable examples thereof include 3-hydroxy-3-methylbutyl, 2,3-dihydroxy-3-methylbutyl, 3,4-dihydroxy-3-methylbutyl, 3-hydroxy-3-ethylpentyl, 2,3-dihydroxy-3-ethylpentyl, 3,4-dihydroxy-3-ethylpentyl, 4-hydroxy-4-methylpentyl, 3,4-dihydroxy-4-methylpentyl and 4,5-dihydroxy-4-methylpentyl groups. Still preferable examples thereof include 3-hydroxy-3-methylbutyl, 3-hydroxy-3-ethylpentyl and 4-hydroxy-4-methylpentyl groups. Among all, a 3-hydroxy-3-methylbutyl group is the most desirable one.

In the present invention, $R_2$ in the general formula (I) is a hydrogen atom or a hydroxyl group and a hydroxyl group is preferable therefor.

Although the confirmation of the compound of the general formula (I) of the present invention is not restricted, a compound of the following general formula (II) is particularly preferable:

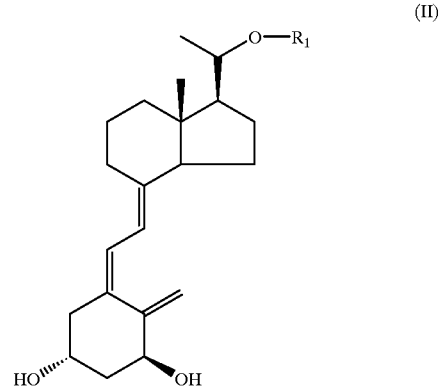

(II)

wherein $R_1$ represents an alkyl group having 1 to 10 carbon atoms and optionally substituted by one or more hydroxyl groups.

As a still preferable compound, one represented by the following formula (III) may be cited:

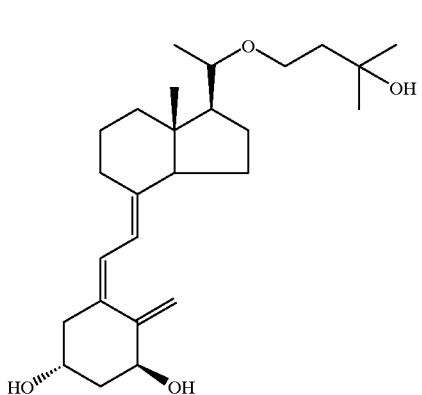

(III)

In addition to the active compound of the general formula (I), the drug of the present invention may contain pharmaceutically acceptable carriers including fillers and auxiliaries with which the active compound can be easily processed into a preparation.

The fillers are not particularly restricted. For example, use can be made of saccharides such as lactose, sucrose, mannitol and sorbitol, cellulose materials and/or excipients such as calcium phosphate.

The auxiliaries may be added if necessary. For example, use can be made of binders, fluidity controlling agents, lubricants and stabilizers.

Examples of the dosage form of the drug of the present invention include oral preparations produced by a conventional method employed for processing vitamin D compounds as well as parenteral preparations such as solutions (for example, injections comprising an aqueous solvent as the main component), noninvasive preparations such as nasal drops, and external preparations such as creams and ointments. Among these preparations, oral preparations and injections are preferable.

It is preferable that the drug of the present invention is administered either orally or systemically as an injection. However, it may be topically administered in the form of an external preparation etc., in some cases.

The dose for an adult of the vitamin D derivative of the present invention usually ranges from 0.01 to 1,000 μg/day, preferably from 0.1 to 100 μg/day and still preferably from 1 to 20 μg/day, though it varies depending on the age, sex, conditions, etc. The dosing frequency is not particularly restricted. Namely, the above-mentioned daily dose may be divided into 1 to 3 portions.

To further illustrate the present invention in greater detail, the following Examples will be given.

In these Examples, 22-oxa-1α,25-dihydroxyvitamin $D_3$ represented by the following formula (III) was used as the active ingredient of the drug of the present invention:

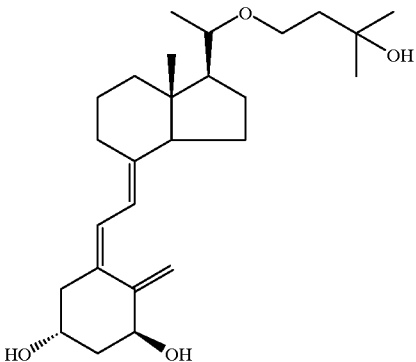

(III)

This 22-oxa-1α,25-dihydroxyvitamin $D_3$ was obtained in accordance with the method described in Japanese Patent Publication No. Hei 3-74656.

EXAMPLE 1

The drug was orally administered in the following manner to nude mice suffering from cachexia and electrolyte abnormality induced by the transplantation of a cell line FA-6 established from human pancreatic tumor.

27 days after the transplantation, the mice were divided into groups each having 5 animals. From the day 28, 6.25 μg/kg body weight of the drug was orally administered 5 times per week continuously for 3 weeks. In the control group to which the vehicle solution alone was administered, the body weight of the test animals was considerably reduced from 21.85±2.42 (g) (on the next day of the administration of the vehicle solution) to 18.97±2.45 (g) (15 days after the administration). In the test group to which the drug was administered 13 times, on the other hand, the body weight before the administration was 21.85±1.79 (g) while that after the administration was 21.45±1.38 (g). These results have proved that the drug significantly suppresses the weight loss of the tumor bearing mice.

In this experiment, the ionized calcium concentration in the whole blood of the control group (n=5) was elevated from 1.93 mmol/L (before the administration) to 2.22 mmol/L (2 weeks thereafter). In the test group (n=5), on the other hand, the ionized calcium concentration in the whole blood was lowered from 1.90 mmol/L (before the administration) to 1.72 mmol/L (after administering 13 times).

Furthermore, all animals in the control group died (average duration of life: 99.5 days), while the test group showed a life prolonged by 1.67 times (166 days on average).

EXAMPLE 2

The drug was intravenously administered in the following manner to nude mice suffering from cachexia and electrolyte abnormality induced by the transplantation of a cell line FA-6 established from human pancreatic tumor.

24 days after the transplantation, the mice were divided into groups each having 5 animals. From the same day, 6.25 μg/kg body weight of the drug was intravenously administered twice or three times per week. In the control group (n=5) to which the vehicle solution alone was administered, the body weight of the test animals was considerably reduced from 20.49 g (before the administration of the vehicle solution) to 17.67 g (18 days after the administration). In the test group (n=5) to which the drug was administered 6 times, on the other hand, the body weight before the administration was 20.62 g while that 18 days after the administration was 22.01 g. These results have proved that the drug significantly suppresses the weight loss of the tumor bearing mice.

In this experiment, the ionized calcium concentration in the whole blood of the control group (n=5) was elevated from 2.06 mmol/L (before the administration) to 2.50 mmol/L in 17 days. In the test group (n=5), on the other hand, the ionized calcium concentration in the whole blood was lowered from 2.04 mmol/L (before the administration) to 1.65 mmol/L (after administraining 6 times).

Thus it has been clarified that the drug of the present invention ameliorates failures in the homeostasis of bodily fluids in association with malignant tumors and the concomitant syndrome of the tumors such as cachexia, thus exerting an effect of prolonging the life. This fact indicates that it is useful as a drug for curing/ameliorating the concomitant syndrome of tumor.

Industrial Applicability

The drug of the present invention containing the vitamin D derivative shows no particularly serious side-effect and patients are in good compliance therewith. Accordingly, it is an efficacious drug for curing/ameliorating the concomitant syndrome of tumor from the viewpoint of quality of life (QOL) too.

I claim:

1. A method for treating cancer cachexia per se without treating cancer in a mammal comprising administering to a mammal in need of such treatment an effective amount of a compound of formula (I):

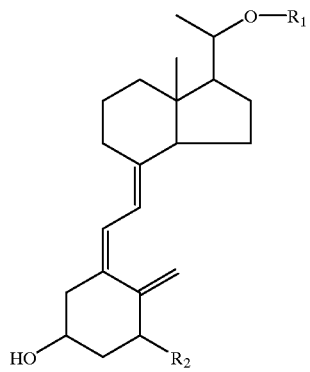

(I)

to treat cachexia, wherein $R_1$ represents an alkyl group having 1 to 10 carbon atoms optionally substituted by one or more hydroxyl groups, and $R_2$ represents a hydrogen atom or a hydroxyl group.

2. A method according to claim 1 wherein said effective amount is in the range of 0.01–1000 μg/day.

3. A method according to claim 1 wherein said effective amount is in the range of 0.01–100 μg/day.

4. A method according to claim 1 wherein said effective amount is in the range of 1–20 μg/day.

5. A method according to claim 1 wherein $R_2$ is a hydroxyl group.

6. A method according to claim 1 wherein the compound administered is represented by formula (II):

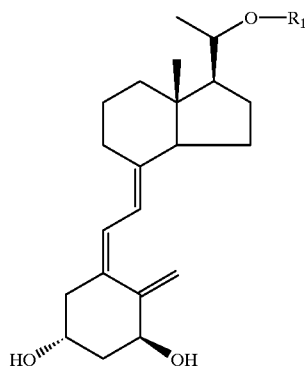

(II)

wherein $R_1$ represents an alkyl group having 1 to 10 carbon atoms and optionally substituted by one or more hydroxyl groups.

7. A method according to claim 1 wherein the compound administered is represented by formula (III):

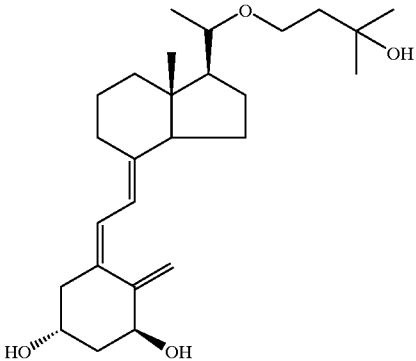

(III)

* * * * *

UNITED STATES PATENT AND TRADEMARK OFFICE
CERTIFICATE OF CORRECTION

PATENT NO. : 5,977,092
DATED : Nov. 2, 1999
INVENTOR(S) : Koichi ENDO

It is certified that error appears in the above-identified patent and that said Letters Patent is hereby corrected as shown below:

On the title page: Item [30], under Foreign Application Priority Data, delete "April 19, 1996" And insert therefore -- April 19, 1994--.

Signed and Sealed this

Nineteenth Day of December, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO.       : 5,977,092
APPLICATION NO.  : 08/727651
DATED            : November 2, 1999
INVENTOR(S)      : Koichi Endo It is certified that error appears in the above-identified patent and that said Letters Patent is hereby corrected as shown below:

Cover page, line [30], under Foreign Application Priority Data, delete "April 19, 1996" And insert therefore -- April 19, 1994--.

Signed and Sealed this

Twenty-second Day of May, 2007

JON W. DUDAS
*Director of the United States Patent and Trademark Office*